United States Patent [19]

Worthington et al.

[11] Patent Number: 4,785,006
[45] Date of Patent: Nov. 15, 1988

[54] FUNGICIDAL COMPOSITIONS CONTAINING PIPERIDINE COMPOUNDS AND USE

[76] Inventors: Paul A. Worthington, 4 Oakhurst Rd., Maidenhead Court Park, Maidenhead, Berkshire; Brian K. Snell, 38 Copse Mead, Woodley, Reading, Berkshire; Paul DeFraine, 5 Salisbury Close, Wokingham, Berkshire; Vivienne M. Anthony, 4 The Croft, Maidenhead, Berkshire, all of England

[21] Appl. No.: 872,686

[22] Filed: Jun. 10, 1986

[30] Foreign Application Priority Data

Jun. 18, 1985 [GB] United Kingdom ................ 8515390
Mar. 5, 1986 [GB] United Kingdom ................ 8605418

[51] Int. Cl.$^4$ ............................................. A01N 43/40
[52] U.S. Cl. .................................. 514/319; 514/238.8; 514/239.2; 514/239.5; 544/173; 544/174; 544/178; 546/205; 546/206
[58] Field of Search ........................ 514/319; 546/206

[56] References Cited

U.S. PATENT DOCUMENTS 4,016,281 4/1977 Jonas et al. ........................ 546/206

FOREIGN PATENT DOCUMENTS 1197849 12/1985 Canada .

Primary Examiner—Robert W. Ramsuer
Attorney, Agent, or Firm—Cushman, Darby & Cushman

[57] ABSTRACT

The invention provides fungicidal compositions comprising as an active ingredient a compound having the general formula (I):

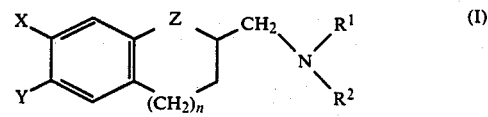

or a stereoisomer thereof wherein X and Y are hydrogen, alkyl, or alkoxy, provided that when one of X and Y is hydrogen the other is not $-C(CH_3)_2R$, where R is hydrogen, methyl or ethyl; Z is carbonyl, or a derivative thereof, or is $-CR^3R^4-$ or $-CR^3OR^4-$ in which $R^3$ and $R^4$ are hydrogen or $C_{1-4}$ alkyl; $R^1$ and $R^2$, which may be the same or different, are hydrogen or $C_{1-4}$ alkyl, or $R^1$ and $R^2$ together with the adjacent N-atom constitute an optionally substituted heterocyclic ring; and n is 0 or 1.

5 Claims, No Drawings

FUNGICIDAL COMPOSITIONS CONTAINING PIPERIDINE COMPOUNDS AND USE

This invention relates to fungicidal, especially plant fungicidal, compositions, to processes for preparing them, and to methods of using them to combat fungi, especially fungal infections in plants. The invention also relates to new compounds per se.

The invention provides fungicidal compositions comprising as an active ingredient a compound having the general formula (I):

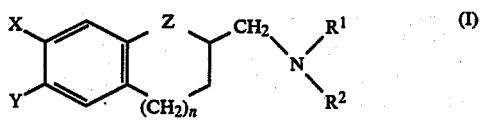

or a stereoisomer thereof wherein X and Y are hydrogen, alkyl, or alkoxy, provided that when one of X and Y is hydrogen the other is not —C(CH$_3$)$_2$R, where R is hydrogen, methyl or ethyl; Z is carbonyl, or a derivative thereof, or is —CR$^3$R$^4$— or —CR$^3$OR$^4$— in which R$^3$ and R$^4$ are hydrogen or C$_{1-4}$ alkyl; R$^1$ and R$^2$, which may be the same or different, are hydrogen or C$_{1-4}$ alkyl, or R$^1$ and R$^2$ together with the adjacent N-atom constitute an optionally substituted heterocyclic ring; and n is 0 or 1.

When R$^1$ and R$^2$ together with the adjacent N-atom represent a heterocyclic ring it may be for example, a piperidine, pyrrolidine, piperazine or morpholine ring which may be optionally substituted by one or more groups such as alkyl (itself optionally substituted) containing one to four carbon atoms, aryl (itself optionally substituted), hydroxy, alkoxy, or aryloxy (itself optionally substituted), or aralkyl (itself optionally substituted).

Derivatives of the carbonyl group in the foregoing statement may include, for example, oximes, oxime ethers, ketals, hydrazones, semicarbazones and thiosemicarbazones.

The invention compositions may alternatively comprise salts of the above compounds of general formula (I) with inorganic or organic acids. Examples of salts are those with hydrochloric, nitric, sulphuric, acetic, 4-toluenesulphonic acid or oxalic acid.

Preferred alkyl groups for R$^3$ and R$^4$ contain from 1 to 6, especially 1 to 4, carbon atoms. When R$^3$ or R$^4$ is alkyl it can be a straight or branched chain alkyl group having to 1 to 6, eg. 1 to 4 carbon atoms; examples are methyl, ethyl, propyl (n- or iso-propyl) and butyl (n-, sec-, iso- or t-butyl).

Preferred compounds are those having —NR$^1$R$^2$ as a 5- or 6-membered heterocyclic ring. Especially preferred ring systems are those of piperidine, 3,5-dimethylpiperidine, 4-phenylpiperidine and 2,6-dimethylmorpholine.

Alkly and alkoxy groups for X and/or Y may be in the form of straight of branched chains and preferably contain 1 to 4 carbon atoms, ie. they may be methyl, ethyl, n-propyl, iso-propyl, n-butyl, sec-butyl, iso-butyl or tert-butyl groups. It is preferred that one of X and Y should be a methoxy group while the other is a hydrogen atom.

Preferred compounds are those in which the group Z is —CH$_2$—, —CHOH— or —CCH$_3$OH.

Compounds falling within the scope of formula (I) are already known from the patent and other literature. For example, U.S. Pat. No. 4,016,281 discloses indanone and tetralone compounds represented by the case where, in formula (I), X and Y are both hydrogen, Z is carbonyl, —NR$^1$R$^2$ is a substituted piperidine ring and n is 0 or 1 respectively. However, these compounds are described in the patent as possessing pharmacological activity only; it has not previously been disclosed that they, or any other of the known compounds falling within the scope of the formula (I), possess fungicidal activity.

Examples of compounds, all conforming to formula (I), which are suitable for incorporation in the compositions of the present invention are shown in Table I.

TABLE I

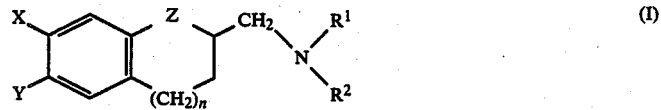

| Compound No. | X | Y | Z | n | NR$^1$R$^2$ | Melting Point (°C.) | Comments |
|---|---|---|---|---|---|---|---|
| 1 | H | H | CO | 0 | —N(morpholine) | 46–48 | |
| 2 | H | H | CO | 1 | —N(2,6-dimethylmorpholine) | 50 | *M |

TABLE I-continued
$$\text{(I)}$$
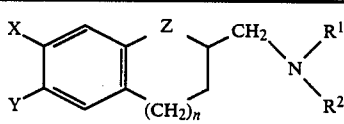
| Compound No. | X | Y | Z | n | NR¹R² | Melting Point (°C.) | Comments |
|---|---|---|---|---|---|---|---|
| 3 | H | H | CHOH | 1 | 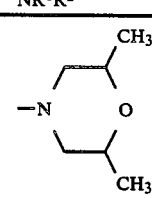 | 117 | °M |
| 4 | H | H | CCH₃OH | 1 | 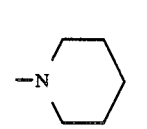 | oil | °M |
| 5 | H | H | CO | 1 | 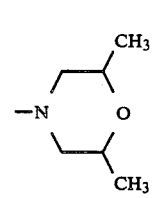 | 30 | |
| 6 | H | OCH₃ | CO | 1 | 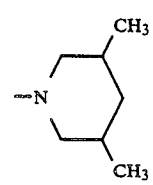 | 110 | *M |
| 7 | H | H | CO | 1 | 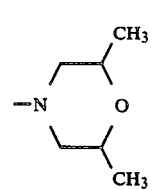 | oil | °M |
| 8 | H | OCH₃ | CHOH | 1 | 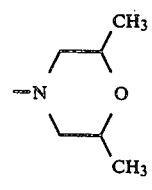 | 113–120 | *M |
| 9 | H | OCH₃ | CCH₃OH | 1 | 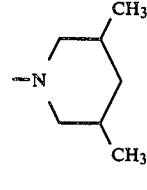 | oil | *M |
| 10 | H | OCH₃ | CO | 1 |  | 79–81 | *M |

TABLE I-continued $$\underset{Y}{\overset{X}{\phantom{X}}} \underset{(CH_2)_n}{\overset{Z}{\phantom{Z}}} \overset{CH_2}{\underset{N}{\phantom{N}}} \overset{R^1}{\underset{R^2}{\phantom{R^2}}} \quad (I)$$

| Compound No. | X | Y | Z | n | NR¹R² | Melting Point (°C.) | Comments |
|---|---|---|---|---|---|---|---|
| 11 | H | OCH₃ | CH₂ | 1 | morpholine with 2,6-diCH₃ | 81–83 | *M |
| 12 | H | OCH₃ | CHOH | 1 | piperidine with 3,5-diCH₃ | oil | *M |
| 13 | H | OCH₃ | CH₂ | 1 | piperidine with 3,5-diCH₃ | oil | *M |
| 14 | H | H | CO | 1 | 4-phenylpiperidine | 80–86 | |
| 15 | H | OCH₃ | CO | 1 | 4-phenylpiperidine | 89–92 | |
| 16 | H | OCH₃ | CHOH | 1 | 4-phenylpiperidine | 133 | trans OH/CH₂NR¹R² |
| 17 | H | H | CH₂ | 1 | 4-phenylpiperidine | oil | |
| 18 | H | OCH₃ | CH₂ | 1 | 4-phenylpiperidine | oil | |
| 19 | H | H | CO | 1 | morpholine with 2,6-diCH₃ | 149–150 | HNO₃ *M salt |
| 20 | H | H | CO | 1 | piperidine | 138–140 | HNO₃ salt |

TABLE I-continued $$\underset{(CH_2)_n}{\overset{X}{\underset{Y}{\bigodot}}} \overset{Z}{\underset{}{\bigodot}} \overset{CH_2}{\underset{}{\bigvee}} \overset{R^1}{\underset{R^2}{N}} \quad (I)$$

| Compound No. | X | Y | Z | n | NR¹R² | Melting Point (°C.) | Comments |
|---|---|---|---|---|---|---|---|
| 21 | CH₃O | H | CO | 1 | piperidinyl | | |
| 22 | CH₃O | H | CHOH | 1 | piperidinyl | | |
| 23 | CH₃O | H | C(CH₃)OH | 1 | piperidinyl | | |
| 24 | CH₃O | H | CH₂ | 1 | piperidinyl | | |
| 25 | CH₃O | H | CHCH₃ | 1 | piperidinyl | | |
| 26 | CH₃O | H | CO | 1 | 2,6-dimethylmorpholinyl | | cis-dimethylmorpholine |
| 27 | CH₃O | H | CHOH | 1 | 2,6-dimethylmorpholinyl | | cis-dimethylmorpholine |
| 28 | CH₃O | H | C(CH₃)OH | 1 | 2,6-dimethylmorpholinyl | | cis-dimethylmorpholine |
| 29 | CH₃O | H | CH₂ | 1 | 2,6-dimethylmorpholinyl | | cis-dimethylmorpholine |

TABLE I-continued $$\text{(I)}$$

Structure: X, Y substituents on benzene ring with Z-CH₂-N(R¹)(R²) and (CH₂)ₙ side chains.

| Compound No. | X | Y | Z | n | NR¹R² | Melting Point (°C.) | Comments |
|---|---|---|---|---|---|---|---|
| 30 | CH₃O | H | CHCH₃ | 1 | cis-2,6-dimethylmorpholino | | cis-dimethylmorpholine |
| 31 | CH₃O | H | CO | 0 | piperidino | | |
| 32 | CH₃O | H | CHOH | 0 | piperidino | | |
| 33 | CH₃O | H | C(CH₃)OH | 0 | piperidino | | |
| 34 | CH₃O | H | CH₂ | 0 | piperidino | | |
| 35 | CH₃O | H | CHCH₃ | 0 | piperidino | | |
| 36 | CH₃O | H | CO | 0 | cis-2,6-dimethylmorpholino | | cis-dimethylmorpholine |
| 37 | CH₃O | H | CHOH | 0 | cis-2,6-dimethylmorpholino | | cis-dimethylmorpholine |
| 38 | CH₃O | H | C(CH₃)OH | 0 | cis-2,6-dimethylmorpholino | | cis-dimethylmorpholine |
| 39 | CH₃O | H | CH₂ | 0 | cis-2,6-dimethylmorpholino | | cis-dimethylmorpholine |

TABLE I-continued $$\text{(I)}$$

Structure: benzene ring with X, Y, Z, $(CH_2)_n$, $CH_2$, N, $R^1$, $R^2$ substituents.

| Compound No. | X | Y | Z | n | $NR^1R^2$ | Melting Point (°C.) | Comments |
|---|---|---|---|---|---|---|---|
| 40 | $CH_3O$ | H | $CHCH_3$ | 0 | 2,6-dimethylmorpholinyl | | cis-dimethyl-morpholine |
| 41 | H | $CH_3O$ | CO | 0 | piperidinyl | | |
| 42 | H | $CH_3O$ | CHOH | 0 | piperidinyl | | |
| 43 | H | $CH_3O$ | $C(CH_3)OH$ | 0 | piperidinyl | | |
| 44 | H | $CH_3O$ | $CH_2$ | 0 | piperidinyl | | |
| 45 | H | $CH_3O$ | $CHCH_3$ | 0 | piperidinyl | | |
| 46 | H | $CH_3O$ | CO | 0 | 2,6-dimethylmorpholinyl | | cis-dimethyl-morpholine |
| 47 | H | $CH_3O$ | CHOH | 0 | 2,6-dimethylmorpholinyl | | cis-dimethyl-morpholine |
| 48 | H | $CH_3O$ | $C(CH_3)OH$ | 0 | 2,6-dimethylmorpholinyl | | cis-dimethyl-morpholine |

TABLE I-continued $$\text{(I)} \quad \underset{Y}{\overset{X}{\bigcirc}} \text{-benzene ring with } Z\text{-CH}(CH_2\text{-}NR^1R^2)\text{-}(CH_2)_n$$

| Compound No. | X | Y | Z | n | NR¹R² | Melting Point (°C.) | Comments |
|---|---|---|---|---|---|---|---|
| 49 | H | $CH_3O$ | $CH_2$ | 0 | 2,6-dimethylmorpholino | | cis-dimethylmorpholine |
| 50 | H | $CH_3O$ | $CHCH_3$ | 0 | 2,6-dimethylmorpholino | | cis-dimethylmorpholine |
| 51 | n-$C_4H_9O$ | H | CO | 1 | piperidino | | |
| 52 | n-$C_4H_9O$ | H | CHOH | 1 | piperidino | | |
| 53 | n-$C_4H_9O$ | H | $C(CH_3)OH$ | 1 | piperidino | | |
| 54 | n-$C_4H_9O$ | H | $CH_2$ | 1 | piperidino | | |
| 55 | n-$C_4H_9O$ | H | $CHCH_3$ | 1 | piperidino | | |
| 56 | n-$C_4H_9O$ | H | CO | 1 | 2,6-dimethylmorpholino | | cis-dimethylmorpholine |
| 57 | n-$C_4H_9O$ | H | CHOH | 1 | 2,6-dimethylmorpholino | | cis-dimethylmorpholine |

TABLE I-continued $$\text{(I)}$$

Structure: benzene ring with X and Y substituents on one side, Z-CH(CH$_2$-NR$^1$R$^2$)-(CH$_2$)$_n$ on the other.

| Compound No. | X | Y | Z | n | NR$^1$R$^2$ | Melting Point (°C.) | Comments |
|---|---|---|---|---|---|---|---|
| 58 | n-C$_4$H$_9$O | H | C(CH$_3$)OH | 1 | 2,6-dimethylmorpholino | | cis-dimethylmorpholine |
| 59 | n-C$_4$H$_9$O | H | CH$_2$ | 1 | 2,6-dimethylmorpholino | | cis-dimethylmorpholine |
| 60 | n-C$_4$H$_9$O | H | CHCH$_3$ | 1 | 2,6-dimethylmorpholino | | cis-dimethylmorpholine |
| 61 | H | n-C$_4$H$_9$O | CO | 1 | piperidino | | |
| 62 | H | n-C$_4$H$_9$O | CHOH | 1 | piperidino | | |
| 63 | H | n-C$_4$H$_9$O | C(CH$_3$)OH | 1 | piperidino | | |
| 64 | H | n-C$_4$H$_9$O | CH$_2$ | 1 | piperidino | | |
| 65 | H | n-C$_4$H$_9$O | CHCH$_3$ | 1 | piperidino | | |
| 66 | H | n-C$_4$H$_9$O | CO | 1 | 2,6-dimethylmorpholino | | cis-dimethylmorpholine |

TABLE I-continued
(I)
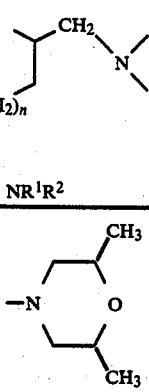
| Compound No. | X | Y | Z | n | NR¹R² | Melting Point (°C.) | Comments |
|---|---|---|---|---|---|---|---|
| 67 | H | n-C$_4$H$_9$O | CHOH | 1 | 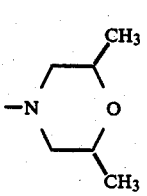 | | cis-dimethyl-morpholine |
| 68 | H | n-C$_4$H$_9$O | C(CH$_3$)OH | 1 | 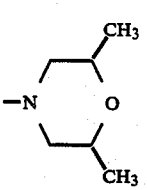 | | cis-dimethyl-morpholine |
| 69 | H | n-C$_4$H$_9$O | CH$_2$ | 1 | 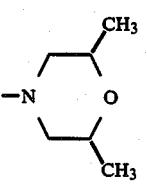 | | cis-dimethyl-morpholine |
| 70 | H | n-C$_4$H$_9$O | CHCH$_3$ | 1 | 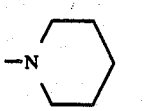 | | cis-dimethyl-morpholine |
| 71 | n-C$_4$H$_9$ | H | CO | 1 | 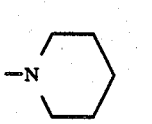 | | |
| 72 | n-C$_4$H$_9$ | H | CHOH | 1 | 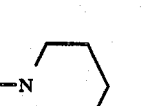 | | |
| 73 | n-C$_4$H$_9$ | H | C(CH$_3$)OH | 1 | 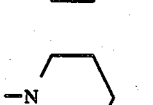 | | |
| 74 | n-C$_4$H$_9$ | H | CH$_2$ | 1 | 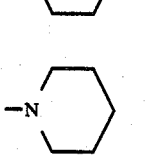 | | |
| 75 | n-C$_4$H$_9$ | H | CHCH$_3$ | 1 | | | |

TABLE I-continued $$\text{(I)}$$

Structure: benzene ring with X and Y on one side, Z-CH$_2$-CH(NR$^1$R$^2$)-... and (CH$_2$)$_n$ bridge.

| Compound No. | X | Y | Z | n | NR$^1$R$^2$ | Melting Point (°C.) | Comments |
|---|---|---|---|---|---|---|---|
| 76 | n-C$_4$H$_9$ | H | CO | 1 | 2,6-dimethylmorpholino | | cis-dimethylmorpholine |
| 77 | n-C$_4$H$_9$ | H | CHOH | 1 | 2,6-dimethylmorpholino | | cis-dimethylmorpholine |
| 78 | n-C$_4$H$_9$ | H | C(CH$_3$)OH | 1 | 2,6-dimethylmorpholino | | cis-dimethylmorpholine |
| 79 | n-C$_4$H$_9$ | H | CH$_2$ | 1 | 2,6-dimethylmorpholino | | cis-dimethylmorpholine |
| 80 | n-C$_4$H$_9$ | H | CHCH$_3$ | 1 | 2,6-dimethylmorpholino | | cis-dimethylmorpholine |
| 81 | H | n-C$_4$H$_9$ | CO | 1 | piperidino | | |
| 82 | H | n-C$_4$H$_9$ | CHOH | 1 | piperidino | | |
| 83 | H | n-C$_4$H$_9$ | C(CH$_3$)OH | 1 | piperidino | | |
| 84 | H | n-C$_4$H$_9$ | CH$_2$ | 1 | piperidino | | |

TABLE I-continued $$\text{(I)} \quad \underset{Y}{\overset{X}{\bigvee}} \overset{Z}{\underset{(CH_2)_n}{\bigvee}} \overset{CH_2}{\underset{N}{\bigvee}} \overset{R^1}{\underset{R^2}{\bigvee}}$$

| Compound No. | X | Y | Z | n | NR¹R² | Melting Point (°C.) | Comments |
|---|---|---|---|---|---|---|---|
| 85 | H | n-C$_4$H$_9$ | CHCH$_3$ | 1 | piperidine | | |
| 86 | H | n-C$_4$H$_9$ | CO | 1 | 2,6-dimethylmorpholine | | cis-dimethylmorpholine |
| 87 | H | n-C$_4$H$_9$ | CHOH | 1 | 2,6-dimethylmorpholine | | cis-dimethylmorpholine |
| 88 | H | n-C$_4$H$_9$ | C(CH$_3$)OH | 1 | 2,6-dimethylmorpholine | | cis-dimethylmorpholine |
| 89 | H | n-C$_4$H$_9$ | CH$_2$ | 1 | 2,6-dimethylmorpholine | | cis-dimethylmorpholine |
| 90 | H | n-C$_4$H$_9$ | CHCH$_3$ | 1 | 2,6-dimethylmorpholine | | cis-dimethylmorpholine |
| 91 | CH$_3$O | H | C(CH$_3$)$_2$ | 1 | piperidine | | |
| 92 | CH$_3$ | H | C(CH$_3$)$_2$ | 1 | 2,6-dimethylmorpholine | | cis-dimethylmorpholine |
| 93 | H | CH$_3$O | C(CH$_3$)$_2$ | 1 | piperidine | | |

TABLE I-continued $$\text{(I)}$$

Structure: X and Y on benzene ring (X top, Y bottom left), Z-CH₂-N(R¹)(R²) substituent, and (CH₂)ₙ linker.

| Compound No. | X | Y | Z | n | NR¹R² | Melting Point (°C.) | Comments |
|---|---|---|---|---|---|---|---|
| 94 | H | CH₃O | C(CH₃)₂ | 1 | 2,6-dimethylmorpholino | | cis-dimethyl-morpholine |
| 95 | n-C₄H₉ | H | C(CH₃)₂ | 1 | piperidino | | |
| 96 | n-C₄H₉ | H | C(CH₃)₂ | 1 | 2,6-dimethylmorpholino | | cis-dimethyl-morpholine |
| 97 | H | n-C₄H₉ | C(CH₃)₂ | 1 | piperidino | | |
| 98 | H | n-C₄H₉ | C(CH₃)₂ | 1 | 2,6-dimethylmorpholino | | cis-dimethyl-morpholine |
| 99 | CH₃O | H | CHOH | 1 | pyrrolidino | | |
| 100 | CH₃O | H | CH₂ | 1 | pyrrolidino | | |
| 101 | H | CH₃O | CHOH | 1 | pyrrolidino | | |
| 102 | H | CH₃O | CH₂ | 1 | pyrrolidino | | |
| 103 | n-C₄H₉ | H | CHOH | 1 | pyrrolidino | | |

TABLE I-continued $$\text{(I)}\quad\underset{Y}{\overset{X}{\bigcirc}}\overset{Z}{\underset{(CH_2)_n}{\bigcirc}}\overset{CH_2}{\underset{}{}}N\overset{R^1}{\underset{R^2}{}}$$

| Compound No. | X | Y | Z | n | NR¹R² | Melting Point (°C.) | Comments |
|---|---|---|---|---|---|---|---|
| 104 | n-C$_4$H$_9$ | H | CH$_2$ | 1 | —N(azetidine) | | |
| 105 | H | n-C$_4$H$_9$ | CHOH | 1 | —N(azetidine) | | |
| 106 | H | n-C$_4$H$_9$ | CH$_2$ | 1 | —N(azetidine) | | |
| 107 | CH$_3$O | H | CHOH | 1 | —N(piperazine)N—Ph | | |
| 108 | CH$_3$O | H | CH$_2$ | 1 | —N(piperazine)N—Ph | | |
| 109 | H | CH$_3$O | CHOH | 1 | —N(piperazine)N—Ph | | |
| 110 | H | CH$_3$O | CH$_2$ | 1 | —N(piperazine)N—Ph | | |
| 111 | n-C$_4$H$_9$ | H | CHOH | 1 | —N(piperazine)N—Ph | | |
| 112 | n-C$_4$H$_9$ | H | CH$_2$ | 1 | —N(piperazine)N—Ph | | |
| 113 | H | n-C$_4$H$_9$ | CHOH | 1 | —N(piperazine)N—Ph | | |
| 114 | H | n-C$_4$H$_9$ | CH$_2$ | 1 | —N(piperazine)N—Ph | | |
| 115 | CH$_3$O | H | n-C$_4$H$_9$CH | 1 | —N(piperidine) | | |

TABLE I-continued $$\text{(I)}$$

Structure (I): benzene ring with X and Y substituents on one side, Z and $CH_2$—CH—$CH_2$—$NR^1R^2$ chain with $(CH_2)_n$ linkage.

| Compound No. | X | Y | Z | n | NR¹R² | Melting Point (°C.) | Comments |
|---|---|---|---|---|---|---|---|
| 116 | H | $CH_3O$ | n-$C_4H_9$CH | 1 | —N(piperidine) | | |
| 117 | $CH_3O$ | H | n-$C_4H_9$CH | 1 | —N(2,6-dimethylmorpholine) | | cis-dimethyl-morpholine |
| 118 | H | $CH_3O$ | n-$C_4H_9$CH | 1 | —N(2,6-dimethylmorpholine) | | cis-dimethyl-morpholine |
| 119 | n-$C_4H_9$ | H | n-$C_4H_9$CH | 1 | —N(piperidine) | | |
| 120 | H | n-$C_4H_9$ | n-$C_4H_9$CH | 1 | —N(piperidine) | | |
| 121 | n-$C_4H_9$ | H | n-$C_4H_9$CH | 1 | —N(2,6-dimethylmorpholine) | | cis-dimethyl-morpholine |
| 122 | H | n-$C_4H_9$ | n-$C_4H_9$CH | 1 | —N(2,6-dimethylmorpholine) | | cis-dimethyl-morpholine |
| 123 | H | H | $CH_2$ | 1 | —N(2,6-dimethylmorpholine) | | cis-dimethyl-morpholine |
| 124 | H | H | $CH_2$ | 1 | —N(3,5-dimethylpiperidine) | | cis-dimethyl-piperidine |

TABLE I-continued

| Compound No. | X | Y | Z | n | NR¹R² | Melting Point (°C.) | Comments |
|---|---|---|---|---|---|---|---|
| 125 | H | H | $C(CH_3)OH$ | 1 | (4,5-dimethylpiperidinyl) | | cis-dimethylpiperidine |
| 126 | H | H | $C(CH_3)OH$ | 1 | (4-phenylpiperidinyl) | | |
| 127 | H | H | $C(CH_3)OH$ | 1 | (3,5-dimethylpiperidinyl) | | cis-dimethylpiperidine |
| 128 | H | H | $C(CH_3)OH$ | 1 | (3-phenylpiperidinyl) | | |

*M signifies a mixture of isomers
Ph signifies a phenyl moiety

Compounds of general formula (I) in which $Z=-CR^3H$, wherein $R^3$ is as defined above, can be prepared by the reduction of compounds of general formula (II) wherein X, Y, n, $R^1$, $R^2$ and $R^3$ are as defined above by hydrogen in the presence of a suitable catalyst, for example 10% palladium on carbon.

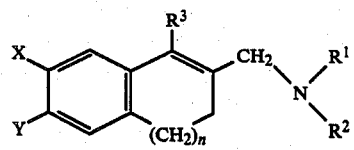

Compounds of general formula (II) can be prepared by treatment of compounds of general formula (IIIa) and (IIIb) wherein X, Y, n, $R^1$, $R^2$ and $R^3$ are as defined above, with an acid (eg. dilute sulphuric acid), preferably in the absence of a solvent and under reflux conditions.

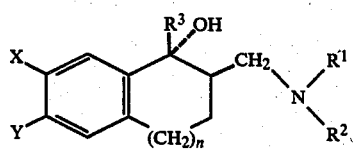

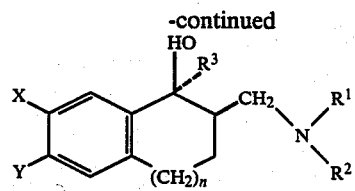

Compounds of general formula (IIIa) and (IIIb) wherein $R^3=H$ can be prepared by reduction of compounds of general formula (IV) (ie. compounds of general formula (I) wherein $Z=C=O$) with the usual reducing agents, for example sodium borohydride or lithium aluminium hydride.

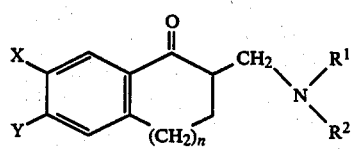

Compounds of general formula (IIIa) and (IIIb) wherein $R^3=C_{1-4}$ alkyl can be prepared by the reaction of compounds of general formula (IV) (ie. compounds of general formula (I) wherein $Z=C=O$) with the appropriate alkyl magnesium halide Grignard reagent (V) or alkyl lithium reagent (VI) in a suitable solvent (for example diethyl ether or tetrahydrofuran), $$R^3MgX \qquad (V)$$

$$R^3Li \qquad (VI)$$

Compounds of general formula (IV) can be prepared by treating a ketone of general formula (VII) with formaldehyde and an amine of general formula $HNR^1R^2$ in the presence of an acidic catalyst under the normal conditions of the Mannich reaction.

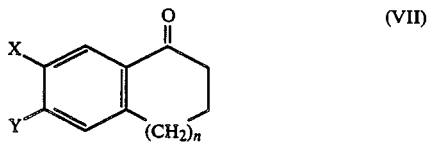

(VII)

Compounds of general formula (VII) can be prepared by cyclisation of variously substituted phenylcarboxylic acids (VIII) by methods set out in the literature (see, for example, Vogel's Textbook of Practical Organic Chemistry. Fourth Edition. IV, 135 pp. 778).

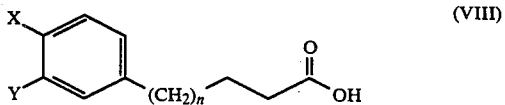

(VIII)

In an alternative process compounds of general formula (I) in which Z represents the group $-CR^3R^4-$ in which both $R^3$ and $R^4$ represent the hydrogen atom can be prepared by reduction of ketones of formula (IV) by a suitable reducing agent, for example by zinc amalgam in the presence of hydrochloric acid, under the usual conditions associated with the Clemmensen Reduction.

Compounds of general formula (I) in which $Z=-CR^3R^4$ wherein $R^3$, $R^4$ are as defined above, can be prepared by reacting a compound of general formula (IXa) or (IXb) where X is a halogen, usually chlorine or bromine, with an organotitanium reagent (X) where X is also a halogen, usually chlorine or bromine, in a convenient solvent such as diethyl ether or tetrahydrofuran.

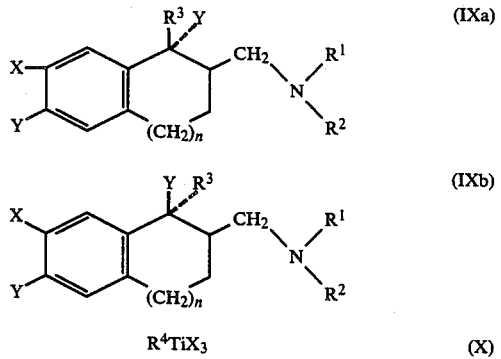

The compounds of general formula (IXa) and (IXb) can be prepared from the alcohols of general formula (IIIa) and (IIIb) using the normal halogenating reagents.

Compounds of general formula (I) in which $Z=CR^3OR^4$, wherein $R^3$ and $R^4$ are as defined above, can be prepared by reacting the sodium salt of compounds of general formula (IIIa) and (IIIb) with an alkyl halide, $R^4X$, where X is a halogen, usually chlorine or bromine, in a convenient solvent such as acetonitrile or dimethylformamide.

Derivatives of the ketones of general formula (IV) such as oximes, oxime ethers, ketals, hydrazones, semicarbazones and thiosemicarbazones can be made by known methods.

Salts of the compounds of general formula (I) can be made by methods set out in the literature.

The compositions of the invention are active particularly against the following diseases: *Puccinia recondita*, *Puccinia striiformis* and other rusts on wheat, *Puccinia hordei, Puccinia striiformis* and other rusts on cereals, apples, vegetables and ornamental plants, *Erysiphe graminis* (powdery mildew) on barley and wheat and other powdery mildews on various hosts such as *Sphaerotheca fuliginea* on cucurbits (eg. cucumber), *Cercospora arachidicola* on peanuts and other Cercospora species on for example sugar beet, bananas and soya beans. *Venturia inaequalis* (scab) on apples. *Pyricularia oryzae* (blast) on rice.

Some of the compounds have also shown a broad range of activities against fungi in vitro. They may have activity against various post-harvest diseases on fruit (eg. *Penicillium digatatum* and *italicum* on oranges and *Gloeosporium musarum* on bananas). Further some of the compounds are active as seed dressings against: *Erysiphe graminis*, Ustilago spp. and Tilletia spp.

The compounds can move acropetally in the plant tissue. Moreover, the compounds can be volatile enough to be active in the vapour phase against fungi on the plant.

They may also be useful as industrial (as opposed to agricultural) fungicides, eg. in the prevention of fungal attack on wood, hides, leather and especially paint films.

The present invention also provides a method of combating fungi, which comprises applying to a plant, to seed of a plant, or to the locus of the plant or seed, a fungicidal composition as hereinbefore defined.

The compositions can be applied in a number of ways, for example they can be applied directly to the foliage of a plant, or they can be applied also to bushes and trees, to seeds or to other medium in which plants, bushes or trees are growing or are to be planted, or they can be sprayed on, dusted on or applied as a cream or paste formulation, or they can be applied as a vapour; or as slow release granules. Application can be to any part of the plant, bush or tree, for example to the foliage, stems, branches or roots, or to soil surrounding the roots, or to the seed before it is planted; or to the soil generally, to paddy water or to hydroponic culture systems. The invention compositions may also be injected into plants or trees and they may also be sprayed onto vegetation using electrodynamic spraying techniques.

The term "plant" as used herein includes seedlings, bushes and trees. Furthermore, the fungicidal method of the invention includes preventative, protectant, prophylactic and eradicant treatment.

The invention embraces various types of fungicidal composition. The type of composition used in any instance will depend upon the circumstances of use envisaged.

The compositions may be in the form of dusting powders or granules comprising the active ingredient and a solid diluent or carrier, for example fillers such as kaolin, bentonite, kieselguhr, dolomite, calcium carbonate, talc, powdered magnesia, Fuller's earth, gypsum, Hewitt's earth, diatomaceous earth and China clay. Such granules can be preformed granules suitable for application to the soil without further treatment. These granules can be made either by impregnating pellets of filler with the active ingredient or by pelleting a mixture of the active ingredient and powdered filler. Compositions for dressing seed, for example, may comprise an agent (for example a mineral oil) for assisting the adhesion of the composition to the seed; alternatively the active ingredient can be formulated for seed dressing purposes using an organic solvent (for example N-methylpyrrolidone or dimethylformamide).

The compositions may also be in the form of dispersible powders, granules or grains comprising a wetting agent to facilitate the dispersion in liquids of the powder or grains which may contain also fillers and suspending agents.

The aqueous dispersions or emulsions may be prepared by dissolving the active ingredient(s) in an organic solvent optionally containing wetting, dispersing or emulsifying agent(s) and then adding the mixture to water which may also contain wetting, dispersing or emulsifying agent(s). Suitable organic solvents are ethylene dichloride, isopropyl alcohol, propylene glycol, diacetone alcohol, toluene, kerosene, methylnaphthalene, the xylenes, trichloroethylene, furfuryl alcohol, tetrahydrofurfuryl alcohol, and glycol ethers (eg. 2-ethoxyethanol and 2-butoxyethanol).

The compositions to be used as sprays may also be in the form of aerosols wherein the formulation is held in a container under pressure in the presence of a propellant, eg. fluorotrichloromethane or dichlorodifluoromethane.

The active compounds can be mixed in the dry state with a pyrotechnic mixture to form a composition suitable for generating in enclosed spaces a smoke containing the compounds.

Alternatively, the active compounds may be used in a micro-encapsulated form. They may aslo be formulated in biodegradable polymeric formulations to obtain a slow, controlled release of the active substance.

By including suitable additives, for example additives for improving the distribution, adhesive power and resistance to rain on treated surfaces, the different compositions can be better adapted for various utilities.

The active compounds can be formulated as mixtures with fertilisers (eg. nitrogen-, potassium- or phosphorus-containing fertilisers). Compositions comprising only granules of fertiliser incorporating, for example coated with, the compound are preferred. Such granules suitably contain up to 25% by weight of the compound. The invention therefore also provides a fertiliser composition comprising a compound of general formula (I) or a salt thereof.

The compositions may also be in the form of liquid preparations for use as dips or sprays which are generally aqueous dispersions or emulsions containing the active ingredient in the presence of one or more surfactants eg. wetting agent(s), dispersing agent(s), emulsifying agent(s) or suspending agent(s); or which are spray formulations of the kind suitable for use in electrodynamic spraying techniques. The foregoing agents can be cationic, anionic or non-ionic agents. Suitable cationic agents are quaternary ammonium compounds, for example cetyltrimethylammonium bromide.

Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butyl-naphthalene sulphonate, and a mixture of sodium diisopropyl- and triisopropylnaphthalene sulphonates).

Suitable non-ionic agents are the condensation products of ethylene oxide with fatty alcohols such as oleyl or cetyl alcohol, or with alkyl phenols such as octyl- or nonyl-phenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carboxymethylcellulose), and the vegetable gums (for example gum acacia and gum tragacanth).

The compositions for use as aqueous dispersions or emulsions are generally supplied in the form of a concentrate containing a high proportion of the active ingredient(s), and the concentrate is to be diluted with water before use. These concentrates often should be able to withstand storage for prolonged periods and after such storage be capable of dilution with water in order to form aqueous preparations which remain homogeneous for a sufficient time to enable them to be applied by conventional and electrodynamic spray equipment. The concentrates may conveniently contain up to 95%, suitably 10-85%, for example 25-60%, by weight of the active ingredient(s). These concentrates suitably contain organic acids (eg. alkaryl or aryl sulphonic acids such as xylenesulphonic acid or dodecyl benzenesulphonic acid) since the presence of such acids can increase the solubility of the active ingredient(s) in the polar solvents often used in the concentrates. The concentrates suitably contain also a high proportion of surfactants so that sufficiently stable emulsions in water can be obtained. After dilution to form aqueous preparations, such preparations may contain varying amounts of the active ingredient(s) depending upon the intended purpose, but an aqueous preparation containing 0.0005% or 0.01% to 10% by weight of active ingredient(s) may be used.

The compositions of this invention can comprise also other compound(s) having biological activity, eg. compounds having similar or complementary fungicidal or plant growth activity or compounds having plant growth regulating, herbicidal or insecticidal activity.

The other fungicidal compound can be, for example, one which is capable of combating ear diseases of cereals (eg. wheat) such as Septoria, Gibberella and Helminthosporium spp., seed and soil borne diseases and downy and powdery mildews on grapes and powdery mildew and scab on apple etc. These mixtures of fungicides can have a broader spectrum of activity than the compound of general formula (I) alone; further the other fungicide can have a synergistic effect on the fungicidal activity of the compound of general formula (I). Examples of the other fungicidal compound are carbendazim, benomyl, thiphanate-methyl, thiabendazole, fuberidazole, etridazole, dichlorofluanid, cymoxanil, oxadixyl, ofurace, metalaxyl, furalaxyl, benalaxyl, fosetyl aluminium, fenarimol, iprodione, procymidone, vinclozolin, penconazole, myclobutanil, R0151297, S3308, pyrazophos, ethirimol, ditalimfos, tridemorph, triforine, nuarimol, triazbutyl, guazatine, propiconazole, prochloraz, flutriafol, chlortriafol i.e. the chemical 1-(1,2,4-triazol-1-yl)-2-(2,4-dichlorophenyl)-hexan-2-ol, DPX H6573(1-((bis-4-fluorophenyl)methylsilyl)-methyl)-1H-1,2,4-triazole, triadimefon, triadimenol, diclobutrazol, fenpropimorph, fenpropindine, chlorozolinate, diniconazol, imazalil, fenfuram, carboxin, oxycarboxin, methfuroxam, dodemorph, BAS 454, blasticidin S, kasugamycin, edifenphos, kitazin P, cycloheximide, phthalide, probenazole, isoprothiolane, tricyclazole, pyroquilan, chlorbenzthiazone, neoasozin, polyoxin D, validamycin A, repronil, flutolanil, pencycuron, diclomezine, phenazin oxide, nickel dimethyldithiocarba-mate, techlofthalam, bitertanol, bupirimate, etaconazole, streptomycin, cypofuram, biloxazol, quinomethionate, dimethirimol, 1-(2-cyano-2-methoxyimino-acetyl)-3-ethyl urea, fenapanil, tolclofosmethyl, pyroxyfur, polyram, maneb, mancozeb, captafol, chlorothalonil, anilazine, thiram, captan, folpet, zineb, propineb, sulphur, dinocap, binapactryl, nitrothalisopropyl, dodine, dithianon, fentin hydroxide, fentin acetate, tecnazene, quintozene, dichloran, copper containing compounds such as copper oxychloride, copper sulphate and Bordeaux mixture, and organomercury compounds.

The compounds of general formula (I) can be mixed with soil, peat or other rooting media for the protection of plants against seed-borne, soil-borne or foliar fungal diseases.

Suitable insecticides which may be incorporated in the composition of the invention include pirimicarb, dimethoate, demeton-s-methyl, formothion, carbaryl, isoprocarb, XMC, BPMC, carbofuran, carbosulfan, diazinon, fenthion, fenitrothion, phenthoate, chlorpyrifos, isoxathion, propaphos, monocrotophos, buprofezin, ethroproxyfen and cycloprothrin.

Plant growth regulating compounds for incorporation with the invention compositions are compounds which control weeds or seedhead formation, or selectively control the growth of less desirable plants (e.g. grasses).

Examples of suitable plant growth regulating compounds for use with the invention compositions and compounds are the gibberellins (e.g. $GA_3$, $GA_4$ or $GA_7$), the auxins (e.g. indoleacetic acid, indolebutyric acid, naphthoxyacetic acid or naphthylacetic acid), the cytokinins (e.g. kinetin, diphenylurea, benzimidazole, benzyladenine or benzylaminopurine), phenoxyacetic acids (e.g. 2,4-D or MCPA), substituted benzoic acids (e.g. triiodobenzoic acid), morphactins (e.g. chlorfluoroecol), maleic hydrazide, glyphosate, glyphosine, long chain fatty alcohols and acids, dikegulac, paclobutrazol, flurprimidol, fluoridamid, mefluidide, substituted quaternary ammonium and phosphonium compounds (e.g. chloromequat chlorphonium or mepiquatchloride), ethephon, carbetamide, methyl-3,6-dichloroanisate, daminozide, asulam, abscisic acid, isopyrimil, 1-(4-chlorophenyl)-4,6-dimethyl-2-oxo-1,2-dihydropyridine-3-carboxylic acid, hydroxybenzonitriles (e.g. bromoxynil), difenzoquat, benzoylprop-ethyl 3,6-dichloropicolinic acid, fenpentezol, inabenfide, triapenthenol and tecnazene.

The following Examples illustrate the invention; the temperatures are given in degrees Centigrade (°C.).

EXAMPLE 1

This Example illustrates the preparation of 6-methoxy-2-(2,6-dimethylmorpholinomethyl)-1,2,3,4-tetrahydronaphthalene (compound No. 11 of Table 1).

6-Methoxy-1,2,3,4-tetrahydronaphthalen-1-one (17.6 g, 0.1 mol), 2,6-dimethylmorpholine hydrochloride (15.1 g, 0.1 mol), and paraformaldehyde (6.0 g, 0.2 mol) were refluxed together in ethanol (50 ml) with concentrated hydrochloric acid (0.25 ml) as a catalyst for 3 hours. The reaction was cooled and poured into water containing concentrated hydrochloric acid (5 ml) and extracted with ether (200 ml). The aqueous solution was cooled in ice and neutralised with sodium hydroxide solution (10%) then extracted with ether (2×200 ml) dried over magnesium sulphate and evaporated under reduced pressure to give a residue which was recrystallised from petrol (60°-80°) to give 6-methoxy-2-(2,6-dimethylmorpholinomethyl)-1,2,3,4-tetrahydronaphthalen-1-one a white crystalline solid (10 g, 33% yield) melting at 110° C.

Zinc amalgam was prepared by stirring zinc (12.5 g, 0.19 mol) with mercuric chloride (1.5 g, 0.0055 mol) in dilute hydrochloric acid (1 ml concentrated HCl in 25 ml water) for 5 minutes, the aqueous solution was decanted and the 6-methoxy-2-(2,6-dimethylmorpholinomethyl)-1,2,3,4-tetrahydronaphthalen-1-one (3.0 g, 0.01 mol) dissolved in concentrated hydrochloric acid (25 ml) was added. The reaction was refluxed for 6 hours and the acid was decanted from the residue which was treated with sodium bicarbonate solution and chloroform. The organic phase was dried over magnesium sulphate and evaporated and the residue recrystallised from petrol (40°-60°) to give a white crystalline solid (600 mgs, 20% yield) melting at 81°-3°, the title compound.

EXAMPLE 2

This Example illustrates the preparation of 6-methoxy-2-(2,6-dimethylmorpholinomethyl)-1,2,3,4-tetrahydronaphthalen-1-ol (compound No. 8 of Table 1).

The 6-methoxy-2-(2,6-dimethylmorpholinomethyl)-1,2,3,4-tetrahydronaphthalen-1-one (2.0 g, 0.006 mol) was dissolved in methanol (50 ml), sodium borohydride (0.25 g, 0.0066 mol) was added to this at room temperature and stirred for 16 hours. The methanol was removed under reduced pressure, extracted with ether (2×100 ml), dried over magnesium sulphate and evaporated under reduced pressure to give a white paste which was recrystallised from petrol (60°-80°) to give the first crop the title compound as a white crystalline solid (350 mgs, 17% yield) melting at 113°-120° C.

EXAMPLE 3

An emulsifiable concentrate is made up by mixing the ingredients, and stirring the mixture until all the constituents are dissolved.

| | |
|---|---|
| Compound No 1 of Table I | 10% |
| Isophorone | 25% |
| Calcium dodecylbenzenesulphonate | 5% |
| Nonylphenolethoxylate (13 moles ethylene oxide) | 10% |
| Alkyl benzenes | 50% |

EXAMPLE 4

The active ingredient is dissolved in methylene dichloride and the resultant liquid sprayed onto the granules of attapulgite clay. The solvent is then allowed to evaporate to produce a granular composition.

| | |
|---|---|
| Compound No 2 of Table I | 5% |
| Attapulgite granules | 95% |

EXAMPLE 5

A composition suitable for use as a seed dressing is prepared by grinding and mixing the three ingredients.

| | |
|---|---|
| Compound No 3 of Table I | 50% |
| Mineral oil | 2% |
| China clay | 48% |

EXAMPLE 6

A dustable powder is prepared by grinding and mixing the active ingredient with talc.

| | |
|---|---|
| Compound No 5 of Table I | 5% |
| Talc | 95% |

EXAMPLE 7

A suspension concentrate is prepared for chemicals which are largely insoluble solids by ball milling, for example, the constituents set out below, to form an aqueous suspension of the ground mixture with water.

| | |
|---|---|
| Compound No 6 of Table I | 40% |
| Sodium lignosulphonate | 10% |
| Bentonite clay | 1% |
| Water | 49% |

This formulation can be used as a spray by diluting into water or applied directly to seed.

EXAMPLE 8

A wettable powder formulation is made by mixing together with ingredients set out below and then grinding the mixture until all are thoroughly mixed.

| | |
|---|---|
| Compound No 8 of Table I | 25% |
| Sodium lauryl sulphate | 2% |
| Sodium lignosulphonate | 5% |
| Silica | 25% |
| China clay | 43% |

EXAMPLE 9

A Col formulation was prepared by ball-milling the constituents set out below and then forming an aqueous suspension of the ground mixture with water.

| | |
|---|---|
| Compound No 10 of Table I | 40% |
| "Dispersol" T | 10% |
| "Lubrol" APN5 | 1% |
| Water | |

EXAMPLE 10

A dispersible powder formulation was made by mixing together the ingredients set out below and then grinding the mixture until all were thoroughly mixed.

| | |
|---|---|
| Compound No 11 of Table I | 25% |
| "Aerosol" OT/B | 2% |
| "Dispersol" A.C. | 5% |
| China clay | 28% |
| Silica | 40% |

In Examples 3 to 10 the proportions of the ingredients given are by weight. The remaining compounds of Tables I were all similarly formulated as for Examples 3 to 10.

There now follows an explanation of the compositions or substances represented by the various Trade Marks and Trade Names mentioned above.

ARAMASOL H:
  a solvent mixture of alkylbenzenes

DISPERSOL T & AC:
  a mixture of sodium sulphate and a condensate of formaldehyde with sodium naphthalene sulphonate LUBROL APN5:
  a condensate of nonyl phenol (1 mole) with naphthalene oxide (5.5 moles)

AEROSOL OT/B:
  dioctyl alkyl naphthalene sulphonate

EXAMPLE 11

The compounds were tested against a variety of mainly foliar fungal diseases of plants. The techniques employed were as follows.

For all tests the plants were grown in John Innes Potting Compost (No. 1 or 2) in 4 cm diameter minipots. The test compounds were formulated either by bead milling with aqueous Dispersol T or as a solution in acetone or acetone/ethanol which was diluted to the required concentration immediately before use. The solutions or suspensions (100 ppm ai.) were sprayed on the foliage and applied to the roots of the plant via the soil. The sprays were applied to maximum retention and the root drenches to a final concentration equivalent to approximately 40 ppm ai./dry soil. Tween 20, to give a final concentration of 0.05%, was added when the sprays were applied to cereals. (a.i. means "active ingredient").

Most were protectant tests where the compound was applied to the soil and roots and to the foliage one or two days before the plant was inoculated with the pathogen. An exception was the test of *Erysiphe graminis* in which the plants were inoculated 24 hours before treatment. The foliar pathogens were applied by spraying as spore suspensions onto the leaves of the test plants.

After inoculation, the plants were placed in an appropriate environment to allow infection to proceed and then incubated until the disease was ready for assessment. The period between inoculation and assessment varied from four to fourteen days according to the disease and the environment.

Disease control was recorded using the following grading system:
  4 = no disease
  3 = trace to 5% of disease on untreated plants
  2 = 6–25% of disease on untreated plants
  1 = 26–59% of disease on untreated plants
  0 = 60–100% of disease on untreated plants The results are shown in Table II.

TABLE II

| COMPOUND NUMBER | PUCCINIA RECONDITA (WHEAT) | VENTURIA INAEQUALIS (APPLES) | CERCOSPORA ARACHIDICOLA (PEANUTS) | ERYSIPHE HORDEI GRAMINIS (BARLEY) | PYRICULARIA ORYZAE (RICE) |
|---|---|---|---|---|---|
| 1 | 0 | 0 | 0 | 2 | 1 |
| 2 | 0 | 0 | 2 | 2 | 1 |
| 3 | 0 | 0 | 0 | 4 | 1 |
| 4 | 0 | 0 | 2 | 4 | 1 |
| 5 | 1 | 0 | 0 | 2 | 1 |
| 6 | 4 | 0 | 0 | 3 | 2 |
| 7 | 4 | 3 | 0 | 4 | 1 |
| 8 | 0 | 4 | 0 | 3 | 0 |
| 9 | 3 | 0 | 2 | 4 | 0 |
| 10 | 4 | 0 | 0 | 3 | 0 |
| 11 | 4 | 1 | 0 | 4 | 0 |
| 12 | 0 | 1 | 0 | 2 | 0 |
| 13 | 4 | 3 | 2 | 4 | 0 |
| 14 | 0 | 0 | 0 | 3 | 0 |
| 16 | 0 | 4 | 0 | 4 | 0 |
| 17 | 0 | 0 | 0 | 4 | 0 |
| 18 | 0 | 0 | 2 | 4 | 0 |

We claim:

1. A fungicidal composition comprising, as an active ingredient, a compound having the general formula:

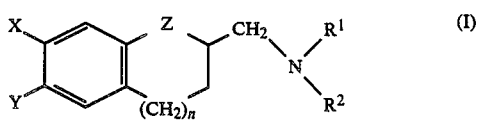

and stereoisomers thereof wherein X and Y are hydrogen, alkyl or alkoxy, provided that at least one of X and Y is alkoxy Z is —$CR^3R^4$— in which $R^3$ and $R^4$ are hydrogen or $C_{1-4}$ alkyl, $R^1$ and $R^2$ together with the adjacent N-atom constitute an aryl substituted piperidine ring; and n is 1; together with a carrier therefor.

2. A composition as claimed in claim 1, wherein in the active compound one of X and Y is a methoxy group while the other is a hydrogen atom.

3. A composition as claimed in claim 1 or claim 2, wherein in the active compound the group —$NR^1R^2$ is a 4-phenylpiperidine ring.

4. A composition as claimed in claim 1 wherein the active compound has the formula

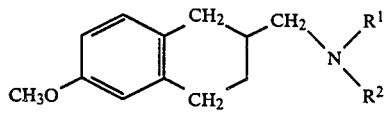

wherein the group —$NR^1R^2$ is a 4-phenylpiperidine ring.

5. A method of combating fungi which comprises applying to a plant, to seed of a plant, or to the locus of a plant or seed, a fungicidal composition as claimed in claim 1.

* * * * *

UNITED STATES PATENT AND TRADEMARK OFFICE
CERTIFICATE OF CORRECTION

PATENT NO. : 4,785,006

DATED : November 15, 1988

INVENTOR(S) : Worthington et al

It is certified that error appears in the above-identified patent and that said Letters Patent is hereby corrected as shown below:

Title page:

Item [73] should read:

--[73] Assignee: Imperial Chemical Industries PLC,
London, England--

Signed and Sealed this

Thirteenth Day of June, 1989

Attest:

DONALD J. QUIGG

*Attesting Officer*

*Commissioner of Patents and Trademarks*